(12) United States Patent
Dikovskiy et al.

(10) Patent No.: US 9,713,610 B2
(45) Date of Patent: Jul. 25, 2017

(54) PHARMACEUTICAL COMPOSITION FOR TREATING GASTRO-OESOPHAGEAL REFLUX DISEASE

(71) Applicants: Alexander Vladimirovich Dikovskiy, Moscow (RU); Leonid Borisovich Lazebnik, Moscow (RU); Dmitry Stanislavovich Bordin, Tver (RU); Elena Valentinovna Belova, Moscow (RU)

(72) Inventors: Alexander Vladimirovich Dikovskiy, Moscow (RU); Leonid Borisovich Lazebnik, Moscow (RU); Dmitry Stanislavovich Bordin, Tver (RU); Elena Valentinovna Belova, Moscow (RU)

(73) Assignee: Alexander Vladimirovich Dikovskiy, Moscow (RU)

( * ) Notice: Subject to any disclaimer, the term of this patent is extended or adjusted under 35 U.S.C. 154(b) by 0 days.

(21) Appl. No.: 14/422,447

(22) PCT Filed: Aug. 22, 2013

(86) PCT No.: PCT/RU2013/000738
§ 371 (c)(1),
(2) Date: Feb. 19, 2015

(87) PCT Pub. No.: WO2014/035295
PCT Pub. Date: Mar. 6, 2014

(65) Prior Publication Data
US 2015/0202192 A1    Jul. 23, 2015

(30) Foreign Application Priority Data
Aug. 30, 2012  (RU) .............................. 2012137067

(51) Int. Cl.
| | |
|---|---|
| A61K 31/4439 | (2006.01) |
| A61K 31/047 | (2006.01) |
| A61K 31/7016 | (2006.01) |
| A61K 31/702 | (2006.01) |
| A61K 31/7032 | (2006.01) |
| A61K 31/715 | (2006.01) |
| A61K 31/732 | (2006.01) |
| A61K 31/733 | (2006.01) |
| A61K 45/06 | (2006.01) |
| A61K 35/00 | (2006.01) |

(52) U.S. Cl.
CPC ........ *A61K 31/4439* (2013.01); *A61K 31/047* (2013.01); *A61K 31/702* (2013.01); *A61K 31/7016* (2013.01); *A61K 31/7032* (2013.01); *A61K 31/715* (2013.01); *A61K 31/732* (2013.01); *A61K 31/733* (2013.01); *A61K 45/06* (2013.01); *A61K 2035/115* (2013.01)

(58) Field of Classification Search
CPC ......................... A61K 31/44; A61K 31/4439
USPC .................................................. 514/338, 333
See application file for complete search history.

(56) References Cited

U.S. PATENT DOCUMENTS

2006/0165824 A1   7/2006  Khambe
2012/0028914 A1*  2/2012  Dikovskiy ........... A61K 31/047
                                                            514/22

FOREIGN PATENT DOCUMENTS

WO        03053221 A2    7/2003

* cited by examiner

*Primary Examiner* — Yong Chu
*Assistant Examiner* — Sonya Wright
(74) *Attorney, Agent, or Firm* — Nadya Reingand

(57) ABSTRACT

The invention relates to medicine and pharmacology, more particularly to drugs, and even more particularly to pharmaceutical compositions for treating gastroesophageal reflux disease (GERD). The pharmaceutical composition for treating GERD contains at least one proton pump inhibitor (PPI) and at least one prebiotic. Also claimed is a method for treating gastroesophageal reflux disease in which it is not necessary to eradicate the presence of *H. pylori* in order to prevent the risks associated with the translocation of said bacteria from the antrum to the body of the stomach. The composition provides for prevention of the translocation of *H. pylori* by means of the colonization of the antrum by *lactobacilli* and the concurrent inhibition of *H. pylori* during PPI therapy. This makes it possible to dispense with the need to detect the bacteria and carry out a course of eradication therapy. The safety of long-term PPI therapy is increased.

15 Claims, No Drawings

PHARMACEUTICAL COMPOSITION FOR TREATING GASTRO-OESOPHAGEAL REFLUX DISEASE

The present patent application claims priority to PCT application No. PCT/RU2013/000738 filed on Aug. 22, 2013, which claims priority to Russian application RU 2012137067 tiled on Aug. 30, 2012.

The invention refers to medicine and pharmacology, namely, to drug products~pharmaceutical compositions (pharmcompositions) for treatment of gastroesophageal reflux disease (GERD).

Gastroesophageal reflux disease is a chronic recurrent disease characterized with regurgitation (reflux) into esophagus of gastric or duodenal contents caused by impaired motor-evacuation function pf esophagogastroduodenal area which are manifested by the symptoms which disturb a patient and/or development of complications (Standards of diagnostics and treatment of acid-dependent and *Helicobacter pylori*-associated diseases (the Fourth Moscow Convention). Experimental and clinical gastroenterology. 2010; 5: pp. 113-118).

The disease falls to the most frequent impairments of gastrointestinal organs. Epidemiological studies have shown that the prevalence of GERD (heartburn and/or regurgitation once a week and more often within the last 12 months) is 10-20% in the countries of Western Europe, North and South America, 5% in Asia, up to 23.6% in Moscow, and 13.3% in Russia (MEGRE's study).

Currently, the accepted view is that both availability and eradication of *H. pylori* are not caused by GERD. However, the negative feedback of *H. pylori's* prevalence in the population and the prevalence of GERD are observed which may indicate a certain "protective" role of *H. pylori*. However, against significant and prolonged drug-induced suppression of acid production with proton pump inhibitors (PPIs), *H. pylori* are distributed from the antrum of the stomach into the gastric corpus (translocation). This can accelerate the processes of losses in special glands of the stomach, leading to the development of atrophic gastritis and, probably, stomach cancer. Therefore, GERD patients who require long-term antisecretory treatment (usually in reflux esophagitis and Barrett's esophagus), are to be diagnosed on the presence of *H. pylori* and, if *H. pylori* is detected, and have them eradicated (Maastricht-4 Consensus (2012), the 4-th Moscow agreement on the diagnosis and treatment of acid-dependent diseases (2010)). The relevance of such approach is associated with high prevalence of *H. pylori* infection in various populations. It is proved that *H. pylori* is present in the stomachs of almost half of the population on Earth (Everhart J. E.//Gastroenterol. Clin. North Amer.-2000.-V.29.-pp. 559-578).

Thus, the need for eradication of *H. pylori* is not due to the treatment of GERD, but is aimed at prevention of the bacteria translocation and, as a consequence, prevention of inflammation spread and atrophy of mucous membrane of the stomach, which in turn prevents the development of stomach cancer.

Currently, standard regimens of *H. pilori* eradication therapy are used which include 2-3 antibiotics taken simultaneously (Maastricht-4 (Malfertheiner P., Megraud F., O'Morain C. A. et al. Management of *Helicobacter pylori* infection—the Maastricht IV./Florence Consensus Report. Gut 2012; 61: 646-664).

Such therapy is often accompanied with development of significant adverse reactions. Because of widespread use of antibiotics in clinical practice (antibiotics form the basis of bacteria eradication treatment regimen), people around the world grow more and more resistant to these antibacterial drugs, with reduced effectiveness of eradication schemes used. In this situation the opportunity of exclusion of antibiotic therapy from treatment of GERD patients is of great clinical importance.

From the prior art, the use of PPIs is known for treatment of GERD (RU 2361574, published on Jul. 20, 2009; RU 2207339, published on Jun. 27, 20036, RU 2184734, published on Jul. 10, 2002).

Since the introduction of PPIs in clinical practice, their application in the world has been increasing each year. In addition to PPIs' increasing application, the number of patients who need long-term administration of PPIs has been growing, too. In this regard, the problem of treatment safety is of particular interest. The potential risks of long intake of PPIs is in many ways linked to the long-term suppression of acid production, digestion impairment, and inactivation of pathogenic organisms that come together with food. That's why PPI therapy is associated with an increased risk of bacterial intestinal infections and development of bacterial overgrowth syndrome.

Reduction of the protective acid barrier allows the bacteria from oral cavity and upper respiratory tract to colonize the stomach and then the small intestine (Parfenov A. I., 2002). For example, it is known that daily intake of 20 mg omeprazole increases in healthy persons the quantity of bacteria in the duodenum and the jejunum by approximately 2 orders of magnitude (S. J. Lewis et al., 1996).

From the prior art the application is known of the compositions containing a proton pump inhibitor (PPI) and a prebiotic for treatment of gastric ulcer and duodenum (RU 2410100, published on Oct. 10, 2010, WO 9403184, published on Feb. 17, 1994). This patent does not reveal a possibility of application of this composition for GERD treatment. The drug dosing regimen (in short courses of 2 to 4 weeks) described in this patent allows to effectively treat ulcer disease, but does not prevent development of atrophic processes and gastric cancer in case of long-term therapy courses (at least 8 weeks) in GERD patients.

The pharmaceutical compositions for GERD treatment are also known which contain a proton pump inhibitor and a second active substance. In this case sodium bicarbonate, Optima Ficus, is used as a second active substance (EP 2201952, published on Oct. 30, 2010, WO 9959612, published on Nov. 25, 1999, EP 2208500, published on Jul. 27, 2010).

The drawback of these compositions is that none of them prevents the development of bacterial overgrowth syndrome and translocation of *H. pylori*, thus no hindering the development of stomach cancer. At the same time, these compositions may aggravate the clinical course of GERD. Thus, for example, neutralization of sodium bicarbonate in the stomach causes regurgitation with stomach contents that can lead to deterioration and/or aggravation of the condition of GERD patients. The long-term administration of drugs containing sodium bicarbonate leads to development of metabolic alkalosis.

The object of this invention is to create an effective combination drug for treatment of GERD which prevents *H. pylori* translocation and development of bacterial overgrowth syndrome.

The technical result of the claimed invention lies in the fact that the problem of translocation of *H. pylori* has been solved through colonization of the antrum with *Lactobacilli* and competitive inhibition of *H. pylori* in the treatment with PPIs which eliminates the need to detect *H. pylori* and conduct bacterial eradication treatment; besides the safety of long-term therapy with PPI's is improved. In this case no atrophy of the gastric mucosa occurs and, consequently, the risk of development of stomach cancer does not increase.

The nature of the claimed invention is that the pharmaceutical composition for treatment of gastroesophageal reflux disease contains at least one proton pump inhibitor and at least one prebiotic with the following content of the composition components, % w/w:

| proton pump inhibitor | 0.05-25 |
|---|---|
| prebiotic | 10-95 |
| excipients | to 100 |

In particular cases of the working of the invention, the composition contains prebiotic of the aliphatic alcohol group, namely, xylitol, sorbitol, lactitol, or contains a prebiotic of the di- and trisaccharide group, namely, lactulose, lactosucrose, melibiose, xylobiose, stachyose, raffinose, or contains a prebiotic of the oligosaccharide group, namely, fructooligosaccharide, galactooligosaccharide, maltooligosaccharide, xylooligosaccharide, isomaltooligosaccharide, gentioligosaccharide, or contains a prebiotic of the polysaccharide group, namely, arabinogalactan, pectins, pullulan, inulin.

In particular cases of the working of the invention, the composition can contain a proton pump inhibitor from the following group: omeprazole, pantoprazole, lansoprazole, rabeprazole, esomeprazole, and dexlansoprazole.

The composition is preferably made in oral dosage form: oral suspension, oral solution, capsules, tablets, powders, sachets, pellets, granules.

The nature of the claimed invention in part of the method is that the method of treatment of gastroesophageal reflux disease is declared, wherein the presence of *H. pylori* does not require its eradication to prevent risks related to translocation of the bacteria from the antrum into the gastric corpus, which is achieved by enteral administration of the pharmaceutical composition "proton pump inhibitor + prebiotic" produced according to any of invention claims 1 to 4 at least once a day for a period determined by the disease form, but not less than 4 weeks.

The composition may contain a proton pump inhibitor, namely, omeprazole in the amount of 10-40 mg, or pantoprazole in the amount of 20-80 mg, or lansoprazole in the amount of 30-60 mg, or rabeprazole in the amount of 10-60 mg, or esomeprazole in the amount of 20-80 mg.

Prebiotics are indigestible food ingredients that contribute to health improvement by selective stimulation of growth and/or metabolic activity of one or more species of bacteria of indigenous microbial population in the large intestine (Gibson G. R., Roberfroid M. B., 1995). Food fibers are not digested in the small intestine under the influence of digestive enzymes and enter in the colon unaltered. In the lower part of the colon oligosaccharides undergo fermentation with *Bifidobacteria* and *Lactobacilli*. This leads to an increase in total bacterial mass, stimulation of the immune system, increase in the intestinal motility and further normalization of the functional activity of the gastrointestinal tract.

The role of a prebiotic (for example, lactulose, fructooligosaccharides, etc.) in achievement of the claimed technical result lies in active stimulation of growth of the patient's indigenous *Lactobacilli* in the antrum and the duodenum, resulting in competitive inhibition of the growth of *Helicobacter pylori*, which is a major factor preventing the translocation and, in some cases, ensuring pathogen eradication. After oral administration of the drug, inside the stomach and duodenum the patient's indigenous *Lactobacilli* begin to actively proliferate (i.e. their overgrowth occurs), with the growth and proliferation of *Helicobacter pylori* inhibited even in the absence of antimicrobial therapy with antibiotics.

The main role in protection against infection belongs to the symbiotic microbial population which ensures colonization resistance of the organism. The colonization resistance means the set of mechanisms which ensure the stability of normal microbial population and prevent colonization of the host organism with pathogens or opportunistic pathogens.

In the studies (Castagliuolo I., Riegler M. F. et al., 1999; Madsen K., Cornish A. et al., 2001) it was shown that *Bifidobacteria* and *Lactobacteria* inhibit adhesion of pathogens, neutralize bacterial toxins and enhance barrier function of the mucous barrier.

*Lactobacilli* are able to prevent the growth of potentially pathogenic bacteria due to competition over substrates, production of antimicrobial agents such as bacteriocins, and stimulation of immunity.

It was shown that *H. pylori* cannot colonize the organisms of gnotobiote mice of BALB/c line infected with *Lactobacillus salivarius*, although sterile mice were more colonized by *H. pylori* with the subsequent development of acute gastritis. Introduction of *L. salivarius* after infection with *H. pylori* led to elimination of colonization.

Most of the works devoted to the studies of the effects of *Lactobacillus* on *H. pylori* in vitro and in vivo were conducted with introduction of exogenous *Lactobacillus* cultures. In the conditions in vitro, the competitive inhibition of the growth of *Helicobacter pylori* was proved.

It was proved in a number of studies that prebiotics stimulate the growth of *Bifidobacteria* and *Lactobacteria*. For example, the work of Probert, H. M., Gibson, G. R., 2002 showed stimulation with prebiotics of the growth of *Bifidobacteria* and *Lactobacteria*.

Increased levels of intestinal *Bifidobacteria* and *Lactobacilli* were observed in stool samples taken from healthy people who received prebiotics.

The increase in the number of *Bifidobacteria* and *Lactobacteria* was also shown in gastrointestinal mucosa of the patients after administration of inulin enriched with fructooligosaccharides in the dosage of 15 g/day for 2 weeks.

The study of prebiotic effects of lactulose administered in the 3 g daily dose in the humans showed a significant increase in the number of *Bifidobacteria* and *Lactobacillus* and decrease in the number of *Clostridium perfringens*, *Bacteroides*, Enterobacteriaceae, and *Streptococcus*.

Proton pump inhibitors (omeprazole, lansoprazole, pantoprazole, rabeprazole and esomeprazole) are the most effective for the treatment of GERD. The therapeutic effect of PPIs is based on lowering the damaging potential of refluctant (the decrease of and modification by the composition via inhibition of acid production) that creates the conditions for termination of symptoms and healing of the damaged esophageal mucosa, PPI are prescribed in the dose of 1-2 times a day 20-30 minutes before meal. The duration of basic treatment course is at least 8 weeks. In reflux esophagitis patients, the treatment duration is extended to 12 weeks. In case of recurrent erosive-ulcerative reflux esophagitis, and Barrett's esophagus, the continuous, supportive treatment with standard PPI doses is recommended; in case of frequently recurring endoscopically negative GERD it is advised to apply continuous supportive treatment with PPI in minimal, but effective dose (to be selected individually);

in case of classical reflux syndrome (endoscopically negative GERD form) "on demand" PPI therapy with symptom control is advised.

The application, for treatment of gastroesophageal reflux disease, of a pharmaceutical composition which contains at least one proton pump inhibitor and at least one prebiotic (with the component content (% w/w) in the composition being 0.05-0.25% of proton pump inhibitor, 10-95% of prebiotic, with excipients up to 100%), according to this invention, provides an unexpected synergy effect of the claimed composition lying in that at the background of PPI administration neither translocation of *H. pylori* from the antrum to the gastric corpus occurs, nor bacterial overgrowth syndrome develops against the background of the long-term PPI intake.

As examples of a practical implementation of the claimed invention, the results of a clinical study of the pharmaceutical composition for GERD treatment are provided, the said composition containing a proton pump inhibitor (PPI) and a prebiotic.

The study included 100 patients with endoscopically negative GERD form, i.e. men and women aged 19 to 50 years old infected with *H. pilori*.

All the patients were divided into 10 groups of 10 persons each, of whom 5 groups (I-V) were experimental ones, while 5 groups (VI-X) were control ones.

In the experimental groups patients received orally the claimed dosage forms based on PPI and a prebiotic; Group I—a composition which contained omeprazole and lactulose as active components; Group II—a composition which contained pantoprazole and lactitol as active components; Group III—a composition which contained lansoprazole and inulin as active components; Group IV—a composition which contained rabeprazole and fructooligosaccharides as active components; Group V—a composition which contained esomeprazole and lactulose as active components.

In the control groups the patients received PPI monotherapy orally: Group VI—omeprazole; Group VII—pantoprazole; Group VIII—lansoprazole; Group IX—rabeprazole and Group X—esomeprazole.

All the patients received treatment on a similar pattern: they received the composition of a proton pump inhibitor and a prebiotic 2 times a day for 56 days.

For incorporation into the pharmaceutical composition, the following therapeutic doses of PPIs were used:

| Proton Pump Inhibitor (PPI) | Daily therapeutic dose (mg) |
|---|---|
| pantoprazole | 20-80 |
| omeprazole; | 10-40 |
| lansoprazole; | 30-60 |
| rabeprazole | 10-60 |
| esomeprazole | 20-80 |

GERD was diagnosed on the basis of the following data: objective clinical data (complaints of heartburn and/or regurgitation discomforting a patient); examination of the mucosa of esophagus with esophagogastroduodenoscopy; accounting of the results of the alginate test (a diagnostic test that assesses the reduction of GERD symptoms after a single administration of the one-time admission of alginic acid preparation with a physical antireflux effect); in some cases, according to indications a 24-hr pH monitoring and esophageal manometry were conducted.

In all patients, before treatment and in 4 weeks (1 month) after completion of the treatment course the biopsy of the antrum and gastric corpus was made for the presence of *Helicobacter pylori*. For HP diagnostics the following was used:

1. Cytological and histological biopsy of mucosa of the antrum and gastric corpus obtained in gastroscopy.
2. Urease test, in which the mucous membrane biopsy material obtained from the antrum and the gastric corpus were examined for the presence of urease, an enzyme specific for *Helicobacter pylori*.

In all patients, quality of life was assessed before treatment and during visits according to the Visual Analog Scale and GSRS questionnaire.

After each patient signed the Informed Consent Form and passed a screening test, he/she was randomized to one of ten therapy groups (each to consist of 10 persons), of whom 5 groups were experimental (where the patients received orally the claimed dosage forms based on PPI and a prebiotic.

The patients kept their diaries in which they made daily records of the time when they took drugs, recorded disease symptom severity according to Likert scale, severity of meteorism, defecation frequency, etc.

Repeated visits were made in 2 and 5 weeks after the treatment start; during the visits treatment efficacy and safety were determined, besides, it was determined if the therapy could be continued. In 56 days (8 weeks) after the therapy start, the patient came to a visit, wherein efficacy and safety of treatment was evaluated and the treatment was terminated. In 11 weeks after the treatment start, the final visit was made which included esophagogastroduodenoscopy with byopsy of the antrum and the gastric corpus for HP detection.

Before and after treatment course (on Day 56) all the patients were subjected to hydrogen breathing test on the presence of bacterial overgrowth syndrome.

As the result of clinical studies show, the claimed pharmaceutical composition used for GERD treatment has high therapeutic efficacy against *H. pylori*, and has a positive effect on the microbial population of duodenum, wherein it stimulates the growth of *Lactobacilli*, and thus prevents development of bacterial overgrowth syndrome which is one of the decisive factors of the composition efficiency. These effects manifested itself through absence of HP translocation from the antrum of the stomach to the gastric corpus, prevention of development of bacterial overgrowth syndrome, and significant reduction of therapy-induced adverse

TABLE 1

| | n = 10 | |
|---|---|---|
| Results of the study patients in group I | before treatment | after treatment |
| Intensity pyrosis on scale Likert, ball | 3.6 ± 0.9 | 1.0 ± 0.5 |
| Intensity regurgitation on scale Likert, ball | 3.4 ± 1.1 | 1.1 ± 0.4 |
| medium term arresting pyrosis, Day | — | 7.9 ± 3.3 |
| medium term arresting regurgitation, Day | — | 7.0 ± 3.0 |
| Presence diarrhea, % | 0 | 0 |
| Presence flatulence, % | 10 | 10 |
| Presence bacterial overgrowth syndrome, % | 10 | 10 |
| release *Helicobacter pylori* in the antrum, % | 100 | 90 |
| release *Helicobacter pylori* in the stomach, % | 20 | 20 |
| Quality of life no VAC, MM | 52.4 ± 22.5 | 85.6 ± 18.8 |
| AE, necessitating discontinuation of therapy, % | — | 0 | reactions. The therapeutic efficacy of the claimed composition concerning main symptoms of GERD is superior in safety to the standard therapy which used PPI alone (tables 1-10).

TABLE 2

| Results of the study patients in group II | n = 10 | |
|---|---|---|
| | before treatment | after treatment |
| Intensity pyrosis on scale Likert, ball | 3.5 ± 0.8 | 1.1 ± 0.4 |
| Intensity regurgitation on scale Likert, ball | 3.4 ± 0.9 | 1.1 ± 0.2 |
| medium term arresting pyrosis, Day | — | 7.4 ± 3.6 |
| medium term arresting regurgitation, Day | — | 8.0 ± 3.1 |
| Presence diarrhea, % | 0 | 10 |
| Presence flatulence, % | 20 | 20 |
| Presence bacterial overgrowth syndrome, % | 10 | 10 |
| release *Helicobacter pylori* in the antrum, % | 100 | 90 |
| release *Helicobacter pylori* in the stomach, % | 30 | 20 |
| Quality of life no VAC, MM | 55.9 ± 19.6 | 83.6 ± 16.4 |

TABLE 3

| Results of the study patients in group III | n = 10 | |
|---|---|---|
| | before treatment | after treatment |
| Intensity pyrosis on scale Likert, ball | 3.7 ± 1.2 | 1.0 ± 0.7 |
| Intensity regurgitation on scale Likert, ball | 3.5 ± 0.9 | 1.0 ± 0.5 |
| medium term arresting pyrosis, Day | — | 7.9 ± 3.5 |
| medium term arresting regurgitation, Day | — | 8.0 ± 3.3 |
| Presence diarrhea, % | 0 | 10 |
| Presence flatulence, % | 10 | 20 |
| Presence bacterial overgrowth syndrome, % | 10 | 10 |
| release *Helicobacter pylori* in the antrum, % | 100 | 90 |
| release *Helicobacter pylori* in the stomach, % | 20 | 20 |
| Quality of life no VAC, MM | 58.2 ± 23.1 | 88.4 ± 15.9 |

TABLE 4

| Results of the study patients in group IV | n = 10 | |
|---|---|---|
| | before treatment | after treatment |
| Intensity pyrosis on scale Likert, ball | 3.5 ± 1.1 | 1.2 ± 0.5 |
| Intensity regurgitation on scale Likert, ball | 3.6 ± 0.7 | 1.0 ± 0.4 |
| medium term arresting pyrosis, Day | — | 7.5 ± 3.2 |
| medium term arresting regurgitation, Day | — | 7.9 ± 3.2 |
| Presence diarrhea, % | 0 | 10 |
| Presence flatulence, % | 10 | 10 |
| Presence bacterial overgrowth syndrome, % | 10 | 10 |
| release *Helicobacter pylori* in the antrum, % | 100 | 90 |
| release *Helicobacter pylori* in the stomach, % | 20 | 20 |
| Quality of life no VAC, MM | 56.2 ± 24.1 | 87.4 ± 16.9 |
| AE, necessitating discontinuation of therapy, % | | 0 |

TABLE 5

| Results of the study patients in group V | n = 10 | |
|---|---|---|
| | before treatment | after treatment |
| Intensity pyrosis on scale Likert, ball | 3.6 ± 0.8 | 1.0 ± 0.8 |
| Intensity regurgitation on scale Likert, ball | 3.7 ± 0.7 | 1.1 ± 0.3 |
| medium term arresting pyrosis, Day | — | 7.8 ± 3.3 |

TABLE 5-continued

| Results of the study patients in group V | n = 10 | |
|---|---|---|
| | before treatment | after treatment |
| medium term arresting regurgitation, Day | — | 8.0 ± 3.0 |
| Presence diarrhea, % | 0 | 0 |
| Presence flatulence, % | 10 | 10 |
| Presence bacterial overgrowth syndrome, % | 10 | 10 |
| release *Helicobacter pylori* in the antrum, % | 100 | 90 |
| release *Helicobacter pylori* in the stomach, % | 30 | 20 |
| Quality of life no VAC, MM | 55.2 ± 23.1 | 85.9 ± 15.7 |
| AE, necessitating discontinuation of therapy, % | | 0 |

TABLE 6

| Results of the study patients in group VI | n = 10 | |
|---|---|---|
| | before treatment | after treatment |
| Intensity pyrosis on scale Likert, ball | 3.6 ± 0.8 | 1.2 ± 0.6 |
| Intensity regurgitation on scale Likert, ball | 3.5 ± 1.2 | 1.1 ± 0.3 |
| medium term arresting pyrosis, Day | — | 7.8 ± 3.5 |
| medium term arresting regurgitation, Day | — | 7.5 ± 3.4 |
| Presence diarrhea, % | 0 | 20 |
| Presence flatulence, % | 20 | 60 |
| Presence bacterial overgrowth syndrome, % | 10 | 50 |
| release *Helicobacter pylori* in the antrum, % | 100 | 100 |
| release *Helicobacter pylori* in the stomach, % | 20 | 70 |
| Quality of life no VAC, MM | 58.1 ± 18.9 | 87.6 ± 21.2 |
| AE, necessitating discontinuation of therapy, % | | 0 |

TABLE 7

| Results of the study patients in group VII | n = 10 | |
|---|---|---|
| | before treatment | after treatment |
| Intensity pyrosis on scale Likert, ball | 3.3 ± 0.5 | 1.0 ± 0.4 |
| Intensity regurgitation on scale Likert, ball | 3.4 ± 1.1 | 1.2 ± 0.3 |
| medium term arresting pyrosis, Day | — | 7.5 ± 3.1 |
| medium term arresting regurgitation, Day | — | 7.6 ± 3.4 |
| Presence diarrhea, % | 0 | 20 |
| Presence flatulence, % | 10 | 50 |
| Presence bacterial overgrowth syndrome, % | 10 | 40 |
| release *Helicobacter pylori* in the antrum, % | 100 | 100 |
| release *Helicobacter pylori* in the stomach, % | 20 | 80 |
| Quality of life no VAC, MM | 58.1 ± 18.9 | 87.6 ± 21.2 |
| AE, necessitating discontinuation of therapy, % | | 0 |

TABLE 8

| Results of the study patients in group VIII | n = 10 | |
|---|---|---|
| | before treatment | after treatment |
| Intensity pyrosis on scale Likert, ball | 3.4 ± 0.7 | 1.1 ± 0.5 |
| Intensity regurgitation on scale Likert, ball | 3.6 ± 1.1 | 1.1 ± 0.2 |
| medium term arresting pyrosis, Day | — | 7.8 ± 3.3 |
| medium term arresting regurgitation, Day | — | 7.7 ± 3.2 |
| Presence diarrhea, % | 0 | 20 |
| Presence flatulence, % | 10 | 60 |
| Presence bacterial overgrowth syndrome, % | 10 | 50 |
| release *Helicobacter pylori* in the antrum, % | 100 | 100 |

TABLE 8-continued

| Results of the study patients in group VIII | n = 10 | |
|---|---|---|
| | before treatment | after treatment |
| release *Helicobacter pylori* in the stomach, % | 20 | 70 |
| Quality of life no VAC, MM | 57.4 ± 17.5 | 84.2 ± 21.5 |
| AE, necessitating discontinuation of therapy, % | | 0 |

TABLE 9

| Results of the study patients in group IX | n = 10 | |
|---|---|---|
| | before treatment | after treatment |
| Intensity pyrosis on scale Likert, ball | 3.6 ± 0.7 | 1.2 ± 0.6 |
| Intensity regurgitation on scale Likert, ball | 3.5 ± 1.1 | 1.1 ± 0.3 |
| medium term arresting pyrosis, Day | — | 7.8 ± 3.5 |
| medium term arresting regurgitation, Day | — | 7.5 ± 3.4 |
| Presence diarrhea, % | 0 | 20 |
| Presence flatulence, % | 20 | 50 |
| Presence bacterial overgrowth syndrome, % | 10 | 40 |
| release *Helicobacter pylori* in the antrum, % | 100 | 100 |
| release *Helicobacter pylori* in the stomach, % | 20 | 80 |
| Quality of life no VAC, MM | 58.5 ± 20.2 | 87.3 ± 19.5 |
| AE, necessitating discontinuation of therapy, % | | 0 |

TABLE 10

| Results of the study patients in group X | n = 10 | |
|---|---|---|
| | before treatment | after treatment |
| Intensity pyrosis on scale Likert, ball | 3.5 ± 0.9 | 1.1 ± 0.2 |
| Intensity regurgitation on scale Likert, ball | 3.6 ± 1.1 | 1.3 ± 0.1 |
| medium term arresting pyrosis, Day | — | 7.7 ± 3.1 |
| medium term arresting regurgitation, Day | — | 7.2 ± 3.1 |
| Presence diarrhea, % | 0 | 20 |
| Presence flatulence, % | 10 | 60 |
| Presence bacterial overgrowth syndrome, % | 10 | 50 |
| release *Helicobacter pylori* in the antrum, % | 100 | 100 |
| release *Helicobacter pylori* in the stomach, % | 20 | 80 |
| Quality of life no VAC, MM | 58.1 ± 18.9 | 87.6 ± 21.2 |
| AE, necessitating discontinuation of therapy, % | | 0 |

The results of clinical trials objectively demonstrate efficacy of GERD treatment with oral administration of the claimed pharmaceutical composition which contains PPI and a prebiotic as active components. The gain in quality of life against the background of the treatment was comparable in groups. It was noted that a prebiotic included in the treatment regimen reduced the frequency of HP translocation from the antrum of the stomach into the gastric corpus through colonization of the antrum of the stomach with *Lactobacilli* and competitive inhibition of *H. pylori*. In addition, the patients treated with a prebiotic manifested the decreased frequency of bacterial overgrowth syndrome owing to stimulation of the growth of normal indigenous microbial population in the patients.

High clinical efficiency and safety due to synergic effects of a proton pump inhibitor and a prebiotic in the upper gastrointestinal tract, the absence of adverse drug reactions shows that the claimed composition is a new promising cure for GERD, which has not been formerly known from the prior art.

The claimed composition can be made at a pharmaceutical plant on standard equipment.

The invention claimed is:

1. A method of treatment of gastroesophageal reflux disease, wherein a presence of *H. pylori* bacteria does not require its eradication to reduce the frequency of translocation of the bacteria from an antrum into a gastric corpus, which is achieved by enteral administration of the pharmaceutical composition "proton pump inhibitor + prebiotic" with the following content of the composition components, % w/w:

| proton pump inhibitor | 0.05-25 |
|---|---|
| prebiotic | 10-95 | at least once a day for a period not less than 2 weeks.

2. A method of treatment of gastroesophageal reflux disease, comprising:
    administering a pharmaceutical composition of a proton pump inhibitor and a prebiotic in the following steps:
    stimulating growth and/or metabolic activity of indigenous *Lactobacilli* in an antrum and a duodenum by delivering a prebiotic to the antrum and the duodenum;
    inhibiting of the growth of *H. pylori*; and
    eliminating translocation of *H. pylori* from the antrum to the gastric corpus by delivering a proton pump inhibitor to an esophageal mucosa.

3. The method of claim 2, wherein
    a ratio by weight between the administered proton pump inhibitor and the prebiotic is from 0.00053 to 0.4.

4. The method of claim 2, wherein the prebiotic comprises an aliphatic alcohol group.

5. The method of claim 2, wherein the prebiotic comprises a di- and trisaccharide group.

6. The method of claim 2, wherein the prebiotic comprises an oligosaccharide group.

7. The method of claim 2, wherein the prebiotic comprises a polysaccharide group.

8. The method of claim 2, wherein the composition is in liquid form of oral suspension or oral solution.

9. The method of claim 2, wherein the composition is in a form of capsules, tablets, powders, sachets, or pellets.

10. The method of claim 2, wherein the proton pump inhibitor is omeprazole.

11. The method of claim 2, wherein the proton pump inhibitor is pantoprazole.

12. The method of claim 2, wherein the proton pump inhibitor is lansoprazole.

13. The method of claim 2, wherein the proton pump inhibitor is rabeprazole.

14. The method of claim 2, wherein the proton pump inhibitor is esomeprazole.

15. The method of claim 2, wherein the proton pump inhibitor is dexlansoprazol.

* * * * *